United States Patent
Sugawa et al.

(10) Patent No.: US 6,187,966 B1
(45) Date of Patent: Feb. 13, 2001

(54) PROCESS FOR PREPARING OPTICALLY ACTIVE ALCOHOLIC COMPOUNDS

(75) Inventors: Tadashi Sugawa, Akashi; Kenji Inoue, Kakogawa; Kazunori Kan, Nishinomiya, all of (JP)

(73) Assignee: Kaneka Corporation, Osaka (JP)

( * ) Notice: Under 35 U.S.C. 154(b), the term of this patent shall be extended for 0 days.

(21) Appl. No.: 09/011,176

(22) PCT Filed: May 30, 1997

(86) PCT No.: PCT/JP97/01844

§ 371 Date: Jul. 5, 1999

§ 102(e) Date: Jul. 5, 1999

(87) PCT Pub. No.: WO97/45391

PCT Pub. Date: Dec. 4, 1997

(30) Foreign Application Priority Data

May 31, 1996 (JP) .................................. 8/160873

(51) Int. Cl.[7] .................................................. C07C 33/46
(52) U.S. Cl. .......................... 568/812; 568/814; 568/880
(58) Field of Search .................................. 568/812, 814, 568/880

(56) References Cited

U.S. PATENT DOCUMENTS 4,284,581 8/1981 Noyori .......................... 260/448 AD

OTHER PUBLICATIONS

Patent Abstracts of Japan, vol. 013, No. 134, Apr. 4, 1989 & JP 63 297333 A, Dec. 5, 1988.
Patent Abstracts of Japan, vol. 096, No. 002, Feb. 29, 1996 & JP 07 252174 A, Oct. 3, 1995.

*Primary Examiner*—Michael L. Shippen

(74) *Attorney, Agent, or Firm*—Pollock, Vande Sande & Amernick

(57) ABSTRACT

A process for preparing optically active alcoholic compounds wherein a carbonyl compound is assymmetrically reduced in an economical and practical manner.

The process comprises treating a prochiral carbonyl compound represented by the general formula (1) with an optically active organoaluminum compound represented by the general formula (2) to conduct asymmetric reduction, thereby preparing an optically active alcoholic compound represented by the general formula (3).

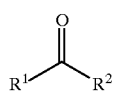

(1)

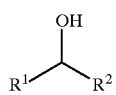

(3)

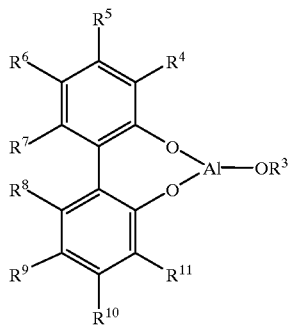

(2)

12 Claims, No Drawings

PROCESS FOR PREPARING OPTICALLY ACTIVE ALCOHOLIC COMPOUNDS

TECHNICAL FIELD

The present invention relates to a process for preparing optically active alcoholic compounds by treating a prochiral carbonyl compound with an optically active diaryloxyaluminum alkoxide to conduct asymmetric reduction. The optically active alcoholic compounds obtained by the process of the present invention, such as (R)-2-chloro-1-(m-hydroxyphenyl) ethanol, are compounds of great value as intermediates for the production of medicines; therefore, the present invention is very useful as a process for preparing the intermediates for the production of medicines.

BACKGROUND ART

As the so-far known practical methods of reducing carbonyl compounds, there may be mentioned Meerwein-Ponndorf-Varley reduction (MPV reduction), the reduction using diisobutylaluminum hydride (DIBAH) and so on.

The MPV reduction is a method of reducing carbonyl compounds using an aluminum trialkoxide, such as Al(OiPr)$_3$, as a reducing agent or a reducing catalyst. This method is in frequent use as an economical method of reducing various ketones and aldehydes, since aluminum trialkoxide used there and alcohol such as isopropanol are inexpensive (Organic Reactions, volume 2, page 178 (1944)).

The technologies for asymmetric reduction of carbonyl compounds using MPV reduction can include, for example, the known method which uses aluminum as a center metal of a catalyst and uses an optically active alcohol as a chiral resource as well as a hydrogen transfer resource; however, its optical purity generally tends to be low and the chiral resource needed is theoretically in an equimolecular amount or more to the substrate (Asymmetric Organic Reactions, Prentice-Hall Inc. (1971)).

As examples of other technologies for asymmetric reduction, there can be exemplified the asymmetric reduction by (−)-isoborneol using a porphyrin complex with aluminum as a catalyst (Journal of Organic Chemistry, volume 55, page 816 (1990)), and the asymmetric reduction by isopropanol using a complex of an optically active alcohol with lanthanoid (Journal of American Chemical Society, volume 15, page 9800, (1993)). Said technologies, however, have problems that the chiral resources and the metal catalysts are expensive.

SUMMARY OF THE INVENTION

In view of the foregoing, it is an object of the present invention to provide a process for preparing optically active alcoholic compounds by asymmetric reduction of a carbonyl compound in an economical and practical manner.

The process for preparing optically active alcoholic compounds according to the present invention comprises treating a prochiral carbonyl compound represented by the general formula (1);

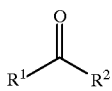

(1)

wherein $R^1$ and $R^2$ are different from each other and represent a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, a substituted or unsubstituted alkoxycarbonyl group containing 1 to 20 carbon atoms, or a cyano group, provided that at least one of $R^1$ and $R^2$ represents a substituted or unsubstituted alkyl group, a substituted or unsubstituted aralkyl group, or a substituted or unsubstituted aryl group; and $R^1$ and $R^2$ may link together and form a ring; with an optically active organoaluminum compound represented by the general formula (2);

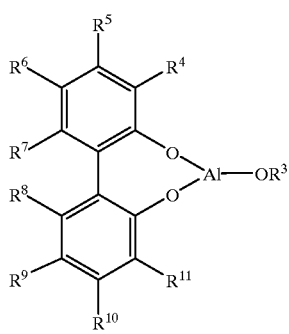

(2)

wherein $R^3$ represents a substituted or unsubstituted alkyl group containing 1 to 20 carbon atoms, or a substituted or unsubstituted aralkyl group containing 7 to 30 carbon atoms; and $R^4$, $R^5$, $R^6$, $R^7$, $R^8$, $R^9$, $R^{10}$ and $R^{11}$ are the same or different from each other and represent a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, a substituted or unsubstituted silyl group, a substituted or unsubstituted amino group, a substituted or unsubstituted alkoxyl group containing 1 to 20 carbon atoms, a cyano group, an alkoxycarbonyl group containing 1 to 20 carbon atoms, a substituted or unsubstituted phosphorus atom, a substituted or unsubstituted sulfur atom, a halogen atom, or a hydrogen atom, and $R^4$, $R^5$, $R^6$, $R^7$, $R^8$, $R^9$, $R^{10}$ or $R^{11}$ may link with each of them and form a substituted or unsubstituted, condensed ring; to conduct asymmetric reduction, thereby preparing an optically active alcoholic compound of the general formula (3);

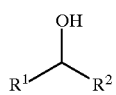

(3)

wherein $R^1$ and $R^2$ are the same as defined above.

DETAILED DESCRIPTION OF THE INVENTION

In the following, the present invention is described in detail.

In the present invention, the above-mentioned $R^1$ and $R^2$ in the general formula (1) always represent different groups from each other: consequently, the alcoholic compound prepared by the process of the present invention necessarily has a chiral carbon atom.

The $R^1$ and $R^2$ represent a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, a substituted or unsubstituted alkoxycarbonyl group containing 1 to 20 carbon atoms, or a cyano group, provided that at least one of $R^1$ and $R^2$ represents a substituted or unsubstituted alkyl group, a substituted or unsubstituted aralkyl group, or a substituted or unsubstituted aryl group. In addition, the $R^1$ and $R^2$ may link together and form a ring.

Said substituent group can include, but is not particularly limited to, for example, a halogen atom, an alkoxycarbonyl group, an amino group, a hydroxyl group, an alkoxyl group, a cyano group, a nitro group, a sulfinyl group, a sulfonyl group, an alkylthio group and the like. It is also possible to be substituted by two or more of such a substituted group.

Said substituted or unsubstituted alkyl group containing 1 to 20 carbon atoms can include, but is not particularly limited to, for example, methyl group, ethyl group, propyl group, isopropyl group, butyl group, isobutyl group, cyclohexyl group, chloromethyl group, dichloromethyl group, trichloromethyl group, carbomethoxymethyl group, cyanomethyl group, nitromethyl group and the like.

Said substituted or unsubstituted aralkyl group containing 7 to 30 carbon atoms can include, but is not particularly limited to, for example, benzyl group, phenylpropyl group, phenylethyl group, p-methoxybenzyl group, p-hydroxybenzyl group and the like.

Said substituted or unsubstituted aryl group containing 6 to 30 carbon atoms can include, but is not particularly limited to, for example, phenyl group, p-hydroxylphenyl group, p-chlorophenyl group, p-nitrophenyl group, naphthyl group and the like.

Said alkoxycarbonyl group containing 1 to 20 carbon atoms can include, for example, methoxycarbonyl group, ethoxycarbonyl group, benzyloxycarbonyl group, t-butoxycarbonyl group and the like.

The above-mentioned carbonyl compound of the general formula (1) can include, but is not particularly limited to, ketones such as acetophenone, propiophenone, cyclohexanone, ethyl acetoacetate, ethyl benzoylformate, ethyl 4-chloroacetoacetate, 2,2,2-trichloroacetophenone, benzoyl cyanide and the like.

The above-mentioned $R^3$ represents a substituted or unsubstituted alkyl group containing 1 to 20 carbon atoms, or a substituted or unsubstituted aralkyl group containing 7 to 30 carbon atoms. As examples of them, there may be mentioned isopropyl group, benzhydryl group, cyclohexyl group, 2,4-dimethyl-3-pentyl group, t-butyl group, ethyl group and the like. Preferred groups are isopropyl and benzhydryl groups.

The above-mentioned $R^4$, $R^5$, $R^6$, $R^7$, $R^8$, $R^9$, $R^{10}$ and $R^{11}$ are the same or different from each other and represent a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, a substituted or unsubstituted silyl group, a substituted or unsubstituted amino group, a substituted or unsubstituted alkoxyl group containing 1 to 20 carbon atoms, a cyano group, an alkoxycarbonyl group containing 1 to 20 carbon atoms, a substituted or unsubstituted phosphorus atom, a substituted or unsubstituted sulfur atom, a halogen atom, or a hydrogen atom. In addition, $R^4$, $R^5$, $R^6$, $R^7$, $R^8$, $R^9$, $R^{10}$ or $R^{11}$ may link with each of them and form a substituted or unsubstituted, condensed ring.

Said substituted or unsubstituted alkyl group containing 1 to 20 carbon atoms is not particularly limited to but includes, for example, methyl group, ethyl group, n-propyl group, isopropyl group, t-butyl group and the like.

Said substituted or unsubstituted aralkyl group containing 7 to 30 carbon atoms is not particularly limited to but includes, for example, benzyl group, phenylpropyl group, α-phenylethyl group, p-methoxybenzyl group, diphenylethyl group and the like.

Said substituted or unsubstituted aryl group containing 6 to 30 carbon atoms is not particularly limited to but includes, for example, phenyl group, p-hydroxyphenyl group, p-chlorophenyl group, p-nitrophenyl group, naphthyl group and the like.

The above-mentioned compound represented by the general formula (2) is not particularly limited but preferred is an optically active (R)-binaphthyl alcohol derivative or (S)-binaphthyl alcohol derivative represented by the general formula (4);

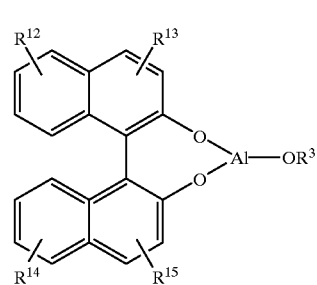

(4)

wherein $R^3$ is the same as defined above; and $R^{12}$, $R^{13}$, $R^{14}$ and $R^{15}$ represent a hydrogen atom, a substituted or unsubstituted alkyl group containing 1 to 20 carbon atoms, a substituted or unsubstituted aryl group containing 6 to 30 carbon atoms, a substituted or unsubstituted aralkyl group containing 7 to 30 carbon atoms, a substituted or unsubstituted silyl group, a substituted or unsubstituted amino group, a substituted or unsubstituted alkoxyl group containing 1 to 20 carbon atoms, a cyano group, an alkoxycarbonyl group containing 1 to 20 carbon atoms, a substituted or unsubstituted phosphorus atom, a substituted or unsubstituted sulfur atom, or a halogen atom.

Said substituted or unsubstituted alkyl group containing 1 to 20 carbon atoms in the $R^{12}$, $R^{13}$, $R^{14}$ and $R^{15}$ is not particularly limited to but includes, for example, methyl group, ethyl group, isopropyl group, t-butyl group and the like.

Said substituted or unsubstituted aralkyl group containing 7 to 30 carbon atoms in the $R^{12}$, $R^{13}$, $R^{14}$ and $R^{15}$ is not particularly limited to but includes, for example, benzyl group, phenylpropyl group, α-phenylethyl group, p-methoxybenzyl group, diphenylethyl group and the like.

Said substituted or unsubstituted aryl group containing 6 to 30 carbon atoms in the $R^{12}$, $R^{13}$, $R^{14}$ and $R^{15}$ is not particularly limited to but includes, for example, phenyl group, p-hydroxyphenyl group, p-chlorophenyl group, p-nitrophenyl group, naphthyl group and the like.

Said substituted or unsubstituted silyl group is not particularly limited to but includes, for example, trimethylsilyl group, t-butyldimethylsilyl group and the like.

Said substituted or unsubstituted amino group is not particularly limited to but includes, for example, dimethylamino group, dibenzylamino group, N-phthaloylamino group and the like.

Said substituted or unsubstituted alkoxyl group containing 1 to 20 carbon atoms is not particularly limited to but includes, for example, methoxy group, ethoxy group, phenoxy group and the like.

Said substituted or unsubstituted alkoxycarbonyl group containing 1 to 20 carbon atoms is not particularly limited to but includes, for example, methoxycarbonyl group, ethoxycarbonyl group, t-butoxycarbonyl group and the like.

Said substituted or unsubstituted phosphorus atom is not particularly limited to but includes, for example, diphenylphosphino group, dimethyphosphino group and the like.

Said substituted or unsubstituted sulfur atom is not particularly limited to but includes, for example, methylthio group, phenylthio group, methylsulfonyl group, phenylsulfonyl group and the like.

Said halogen atom is not particularly limited to but includes, for example, fluorine atom, chlorine atom, bromine atom, iodine atom and the like.

The compounds shown below and the like can be mentioned as a typical concrete example of the compound represented by the general formula (4).

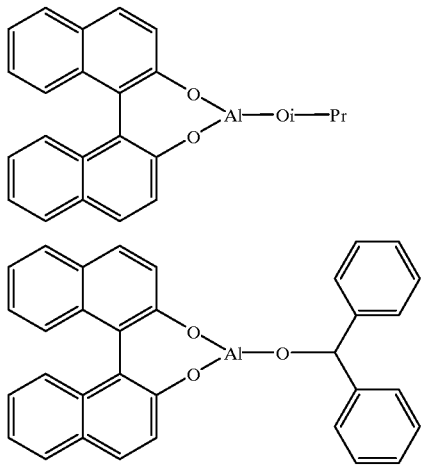

The reaction of the present invention is preferably carried out in the presence of an alcoholic compound represented by the general formula (5);

$$R^3OH \quad (5)$$

wherein $R^3$ represents a substituted or unsubstituted alkyl group containing 1 to 20 carbon atoms, a substituted or unsubstituted aralkyl group containing 7 to 30 carbon atoms, or a substituted or unsubstituted aryl group containing 6 to 30 carbon atoms. As a example of the $R^3$, there can be exemplified the above-mentioned groups of that in the compound of the general formula (4).

Said alcoholic compound of the general formula (5) is not particularly limited to but includes, for example, isopropanol, benzhydrol, cyclohexanol, 2,4-dimethyl-3-pentanol, ethanol and the like. Among them, isopropanol and benzhydrol are more preferable.

The reaction of the present invention can also be carried out by treating with a reducing agent prepared by treating an aluminum compound of the general formula (6);

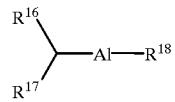

wherein $R^{16}$, $R^{17}$ and $R^{18}$ are the same or different from each other and represent an alkyl group containing 1 to 20 carbon atoms, an aralkyl group containing 7 to 30 carbon atoms, an aryl group containing 6 to 30 carbon atoms, an alkoxyl group containing 1 to 20 carbon atoms, or a hydrogen atom; with an optically active bisalcohol derivative represented by the general formula (7);

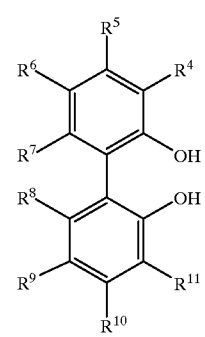

wherein $R^4$, $R^5$, $R^6$, $R^7$, $R^8$, $R^9$, $R^{10}$ and $R^{11}$ are the same as defined above;
and with an alcoholic compound represented by the general formula (5);

$$R^3OH \quad (5)$$

wherein $R^3$ is the same as defined above.

Said alkyl group containing 1 to 20 carbon atoms in the $R^{10}$, $R^{17}$ and $R^{18}$ is not particularly limited to but includes, for example, isobutyl group, ethyl group, cyclohexyl group, methyl group and the like. Among them, isobutyl group is preferable.

Said aralkyl group containing 7 to 30 carbon atoms in the $R^{16}$, $R^{17}$ and $R^{18}$ is not particularly limited to but includes, for example, 2-phenylpropyl group, 2,2-diphenylethyl group, benzyl group and the like.

Said aryl group containing 6 to 30 carbon atoms in the $R^{16}$, $R^{17}$ and $R^{19}$ is not particularly limited to but includes, for example, phenyl-group, p-methoxyphenyl group and the like.

Said alkoxyl group containing 1 to 20 carbon atoms in the $R^{16}$, $R^{17}$ and $R^{18}$ is not particularly limited to but includes, for example, isopropoxy group, ethoxy group and the like.

As a concrete example of the compounds represented by the general formula (6), there can be exemplified diisobutylaluminum hydride (DIBAH), triisobutylaluminum, aluminum triisopropoxide, triethylaluminum, aluminum hydride and the like. Among them, diisobutylaluminum hydride (DIBAH), triisobutylaluminum and aluminum triisopropoxide are more preferable.

As a example of said $R^4$, $R^5$, $R^6$, $R^7$, $R^8$, $R^9$, $R^{10}$ and $R^{11}$ in the compound represented by the general formula (7), there can be exemplified the above-mentioned groups of those in the compound represented by the general formula (2).

As concrete examples of the compounds represented by the general formula (7), there can be exemplified optically active (S)-1,1'-bi-2-naphthol, (R)-1,1'-bi-2-naphthol, (R)-6,6'-dibromo-1,1'-bi-2-naphthol, (S)-6,6'-dibromo-1,1'-bi-2-naphthol and the like.

The method for preparing the above-mentioned compounds represented by the general formula (2) or (4) is not particularly limited, and various methods can be employed.

As a substrate which can be applied to the process of the present invention, there can be mentioned, for example, the above-mentioned compound represented by the general formula (1). Among all, preferred is a prochiral α-haloketone derivative represented by the general formula (8);

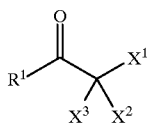

(8)

wherein $R^1$ is the same as defined above; and $X^1$, $X^2$, $X^3$ are the same or different from each other and represent a halogen atom, a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, or a hydrogen atom, provided that at least one of $X^1$, $X^2$ and $X^3$ is a halogen atom.

As a example of said halogen atom in the $X^1$, $X^2$ and $X^3$, there can be exemplified fluorine atom, chlorine atom, bromine atom, iodine atom and the like.

As concrete examples of the compound represented by the general formula (8), there can be exemplified phenacyl chloride, m-chlorophenacyl chloride, ethyl 4-chloroacetoacetate, 2,2,2-trichloroacetophenone, 2,2-dichloroacetophenone and the like.

The process for preparing an optically active alcoholic compound according to the present invention can be carried out, for example, in the following manner.

At first, an aluminum compound of the general formula (6) is reacted with an optically active biaryl derivative of the general formula (7), and then is reacted with an alcoholic compound of the general formula (5) to prepare, for example, a solution of a reducing agent of the general formula (2).

To the obtained solution is added a carbonyl compound as a substrate to carry out reduction reaction by stirring. After-treatment, isolation and the like are carried out in a conventional manner to obtain an alcoholic compound as a reduction product.

As the solvent used in the above-mentioned reaction is not particularly limited to but includes, for example, hexane, toluene, tetrahydrofuran, dimethoxyethane and the like.

There is no particular limitation on a proportion of the aluminum compound of the general formula (6), but it can be used in a proportion of 0.001 to 5 molar equivalents to the carbonyl compound of the general formula (1), and preferably in a proportion of 0.01 to 1 molar equivalents in view of cost and reaction rate.

The optically active biaryl derivative of the general formula (7) can be used in a proportion of 1 to 5 molar equivalents, and preferably 1 to 1.2 molar equivalents, to the aluminum compound of the general formula (6).

There is no particular limitation on a proportion of the alcoholic compound of the general formula (5), provided that it is not less than 1 molar equivalent to the aluminum compound of the general formula (6). It is preferred to be 1 to 50 molar equivalents, and more preferably 1 to 10 molar equivalents.

The reaction of the aluminum compound of the general formula (6) with the optically active biaryl derivative of the general formula (7) and with the alcoholic compound of the general formula (5) can be carried out, for example, by adding successively an optically active biaryl derivative of the general formula (7) and an alcoholic compound of the general formula (5) into a solution of an aluminum compound of the general formula (6) in toluene, hexane, tetrahydrofuran or the like, and then stirring.

As examples of the solvent used in the above-mentioned reaction, in addition to the above-mentioned solvents, there can be also exemplified ethyl acetate, acetonitrile, methylene chloride and the like.

There is no particular limitation on an addition condition in the above-mentioned reaction. It is preferred to be carried out, for example, at −20 to 60° C., and more preferably at 0 to 40° C. There is no particular limitation on a stirring condition. It is preferred to be carried out, for example, at 0 to 30° C. for 0.5 to 10 hours.

The method of preparing the above-mentioned reducing agent is not limited to the above-mentioned method. Various methods can be employed which can prepare the compound of the general formula (2).

The carbonyl compound of the general formula (1) is then added to the reaction system and stirred to carry out reduction reaction of the carbonyl compound of the general formula (1). The reduction reaction is preferably carried out at 0 to 100° C., and more preferably at 10 to 60° C.

The following compounds and the like can be exemplified as examples of the optically active alcoholic compound which can be obtained by the process of the present invention.

(S)-2-chloro-1-phenylethanol, (S)-2-chloro-1-(m-chlorophenyl)ethanol (R)-2-chloro-1-(m-chlorophenyl) ethanol.

BEST MODE FOR CARRYING OUT THE INVENTION

The following examples are intended to describe the present invention in further details, but the scope of the present invention is not limited to these examples.

EXAMPLE 1

Preparation of (S)-2-chloro-1-phenylethanol

To 0.5 ml (0.5 mmol) of hexane solution of triisobutylaluminum (1.0 M) was added a slurry solution of 143 mg (0.5 mmol) of (R)-1,1'-bi-2-naphthol in 10 ml of toluene at room temperature, and the mixture was then stirred at room temperature for 30 minutes. Thereto 1.52 ml (20 mmol) of 2-propanol was added and the mixture was stirred further at room temperature for 30 minutes. Thereto 1.55 g (10 mmol) of phenacyl chloride was added and the mixture was stirred further at room temperature for 20 hours. To the mixture were added 2 ml of 1N hydrochloric acid and 20 ml of water to conduct hydrolysis. The mixture was extracted with ethyl acetate and concentrated to obtain 1.739 g of an oily product. The obtained oil was purified by silica gel column chromatography (hexane/ethyl acetate) to obtain 1.159 g (7.4 mmol, 74% yield) of 2-chloro-1-phenylethanol. The optical purity, which was analyzed by HPLC optical resolution column of the above product, showed that (S)-2-chloro-1-phenylethanol was produced selectively in 67.2% ee.

EXAMPLE 2

Preparation of (S)-2-chloro-1-phenylethanol

After preparing the reducing agent by the same method as described in Example 1. 1.55 g (10 mmol) of phenacyl chloride was added to the reducing agent and the mixture was stirred at 50° C. for 2 hours. To the mixture were added 2 ml of 1N hydrochloric acid and 20 ml of water to conduct hydrolysis. The mixture was extracted with ethyl acetate and concentrated to obtain an oily product. The obtained oil was analyzed by HPLC.

2-chloro-1-phenylethanol: 96.3% yield (S)-2-chloro-1-phenylethanol: optical yield of 63.2%ee

EXAMPLE 3

Preparation of (S)-2-chloro-1-phenylethanol

To 0.5 ml (0.5 mmol) of hexane solution of triisobutylaluminum (1.0 M) was added a slurry solution of 143 mg (0.5 mmol) of (R)-1,1'-bi-2-naphthol in 10 ml of toluene at room temperature, and the mixture was stirred at room temperature for 30 minutes. Thereto 1.84 g (20 mmol) of benzhydrol was added and the mixture was stirred further at room temperature for 30 minutes. Thereto 1.55 g (10 mmol) of phenacyl chloride was added and the mixture was stirred further at room temperature for 2 hours. The after-treatment and the analysis of the product were then carried out in the same manner as described in Example 2.

2-chloro-1-phenylethanol: 93.0% yield (S)-2-chloro-1-phenylethanol: optical yield of 71.5% ee

EXAMPLE 4

Preparation of (S)-2-chloro-1-phenylethanol

To a slurry solution of 143 mg (0.5 mmol) of (R)-1,1'-bi-2-naphthol in 10 ml of toluene was added 0.5 ml (0.5 mmol) of toluene solution of diisobutylaluminum hydride (1.0 M) at room temperature, and the mixture was stirred at room temperature for 1 hour. Thereto 1.52 ml (20 mmol) of 2-propanol was added and the mixture was stirred further at room temperature for 30 minutes. Thereto 1.55 g (10 mmol) of phenacyl chloride was added and the mixture was stirred at 50° C. for 4 hours. To the mixture were added 6 ml of 1N hydrochloric acid and 20 ml of water to conduct hydrolysis. The mixture was extracted with ethyl acetate and concentrated to obtain an oily product. The after-treatment and the analysis of the product were then carried out in the same manner as described in Example 2.

2-chloro-1-phenylethanol: 91.2% yield (S)-2-chloro-1-phenylethanol: optical yield of 65%ee

EXAMPLE 5

Preparation of (S)-2-chloro-1-phenylethanol

To a slurry solution of 143 mg (0.5 mmol) of (R)-1,1'-bi-2-naphthol in 10 ml of toluene was added 102 mg (0.5 mmol) of aluminum triisopropoxide at room temperature, and the mixture was stirred at room temperature for 20 minutes and further at 50° C. for 1 hour. Thereto 1.52 ml (20 mmol) of 2-propanol was added and the mixture was stirred further at room temperature for 30 minutes. Thereto 1.55 g (10 mmol) of phenacyl chloride was added and the mixture was further stirred at 50° C. for 4 hours. To the mixture were added 2 ml of 1N hydrochloric acid and 20 ml of water to conduct hydrolysis. The mixture was extracted with ethyl acetate and concentrated to obtain an oily product. The after-treatment and the analysis of the product were then carried out in the same manner as described in Example 2.

2-chloro-1-phenylethanol: 66.2% yield (S)-2-chloro-1-phenylethanol optical yield of 62%ee

EXAMPLE 6

Preparation of (S)-2-chloro-1-(m-chlorophenyl)ethanol

To a slurry solution of 143 mg (0.5 mmol) of (R)-1,1'-bi-2-naphthol in 10 ml of toluene was added 0.5 ml (0.5 mmol) of a 1.0 M hexane solution of triisobutylaluminum at room temperature, and the mixture was stirred at room temperature for 30 minutes. Thereto 1.84 g (20 mmol) of benzhydrol was added and the mixture was stirred further at room temperature for 30 minutes. Thereto 1.89 g (10 mmol) of m-chlorophenacyl chloride was added and the mixture was stirred further at room temperature for 4 hours. To the mixture were added 2 ml of 1N hydrochloric acid and 20 ml of water to conduct hydrolysis. The mixture was extracted with ethyl acetate and concentrated to obtain 4.135 g of an oily product. The oil was purified by silica gel column chromatography (hexane / ethyl acetate) to obtain 1.44 g (7.5 mmol, 75% yield) of 2-chloro-1-(m-chlorophenyl) ethanol. The analyzed result of the optical purity of the obtained product by using HPLC optical resolution column showed that (S)-2-chloro-1-(m-chlorophenyl) ethanol was produced selectively in 77.0% ee.

EXAMPLE 7

Preparation of (S)-2-chloro-1-(m-chlorophenyl)ethanol

To a slurry solution of 143 mg (0.5 mmol) of (R)-1,1'-bi-2-naphthol in 10 ml of toluene was added 0.5 ml (0.5 mmol) of a 1.0 M hexane solution of triisobutylaluminum at room temperature, and the mixture was stirred at room temperature for 30 minutes. Thereto 1.52 ml (20 mmol) of 2-propanol was added and the mixture was stirred further at room temperature for 30 minutes. Thereto 1.89 g (10 mmol) of m-chlorophenacyl chloride was added and the mixture was stirred further at 50° C. for 4 hours. To the mixture were added 2 ml of 1N hydrochloric acid and 20 ml of water to conduct hydrolysis. The mixture was extracted with ethyl acetate and concentrated to obtain 2.424 g of an oily product. The obtained oil was analyzed by HPLC.

2-chloro-1-(m-chlorophenyl)ethanol: 78.4% yield (S)-2-chloro-1-(m-chlorophenyl)ethanol: optical yield of 63.3% ee

EXAMPLE 8

Preparation of (R)-2-chloro-1-(m-chlorophenyl)ethanol

To a slurry solution of 143 mg (0.5 mmol) of (S)-1,1'-bi-2-naphthol in 10 ml of toluene was added 0.5 ml (0.5 mmol) of a 1.0 M hexane solution of triisobutylaluminum at room temperature, and the mixture was stirred at room temperature for 30 minutes. Thereto 1.52 ml (20 mmol) of 2-propanol was added and the mixture was stirred at room temperature for 30 minutes. Thereto 1.89 g (10 mmol) of m-chlorophenacyl chloride was added and the mixture was stirred further at 50° C. for 4 hours. To the mixture were added 2 ml of 1N hydrochloric acid and 20 ml of water to conduct hydrolysis. The mixture was extracted with ethyl acetate and concentrated to obtain 2.310 g of an oily product. The obtained oil was analyzed by HPLC.

2-chloro-1-(m-chlorophenyl)ethanol: 75.3% yield (R)-2-chloro-1-(m-chlorophenyl)ethanol optical yield of 62.0% ee

INDUSTRIAL APPLICABILITY

The present invention, being constructed by the above, makes it possible to prepare, in an economical and practical manner, optically active alcoholic compounds which are useful intermediates for synthesizing medicines.

What is claimed is:

1. A process for preparing optically active alcoholic compounds, which comprises treating a prochiral carbonyl compound represented by the general formula (1);

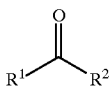
(1)

wherein $R^1$ and $R^2$ are different from each other and represent a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, a substituted or unsubstituted alkoxycarbonyl group containing 1 to 20 carbon atoms, or a cyano group, provided that at least one of $R^1$ and $R^2$ represents a substituted or unsubstituted alkyl group, a substituted or unsubstituted aralkyl group, or a substituted or unsubstituted aryl group; and $R^1$ and $R^2$ may link together and form a ring;

with an optically active organoaluminum compound represented by the general formula (2);

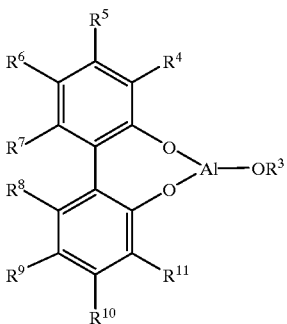
(2)

wherein $R^3$ represents a substituted or unsubstituted alkyl group containing 1 to 20 carbon atoms, or a substituted or unsubstituted aralkyl group containing 7 to 30 carbon atoms; and $R^4$, $R^5$, $R^6$, $R^7$, $R^8$, $R^9$, $R^{10}$ and $R^{11}$ are the same or different from each other and represent a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, a substituted or unsubstituted silyl group, a substituted or unsubstituted amino group, a substituted or unsubstituted alkoxyl group containing 1 to 20 carbon atoms, a cyano group, an alkoxycarbonyl group containing 1 to 20 carbon atoms, a substituted or unsubstituted phosphorus atom, a substituted or unsubstituted sulfur atom, a halogen atom, or a hydrogen atom, and $R^4$, $R^5$, $R^6$, $R^7$, $R^8$, $R^9$, $R^{10}$ or $R^{11}$ may link with each of them and form a substituted or unsubstituted, condensed ring;

to conduct asymmetric reduction, thereby preparing an optically active alcoholic compound of the general formula (3);

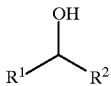
(3)

wherein $R^1$ and $R^2$ are the same as defined above.

2. The process for preparing optically active alcoholic compounds according to claim 1, wherein the organoaluminum compound represented by the general formula (2) is an optically active (R)-binaphthyl alcohol derivative or (S)-binaphthyl alcohol derivative represented by the general formula (4);

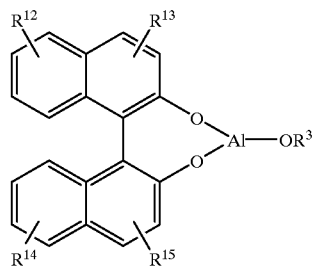
(4)

wherein $R^3$ represents a substituted or unsubstituted alkyl group containing 1 to 20 carbon atoms, or a substituted or unsubstituted aralkyl group containing 7 to 30 carbon atoms; and $R^{12}$, $R^{13}$, $R^{14}$ and $R^{15}$ represent a hydrogen atom, a substituted or unsubstituted alkyl group containing 1 to 20 carbon atoms, a substituted or unsubstituted aryl group containing 6 to 30 carbon atoms, a substituted or unsubstituted aralkyl group containing 7 to 30 carbon atoms, a substituted or unsubstituted silyl group, a substituted or unsubstituted amino group, a substituted or unsubstituted alkoxyl group containing 1 to 20 carbon atoms, a cyano group, an alkoxycarbonyl group containing 1 to 20 carbon atoms, a substituted or unsubstituted phosphorus atom, a substituted or unsubstituted sulfur atom, or a halogen atom.

3. The process for preparing optically active alcoholic compounds according to claim 1, wherein the reduction reaction is carried out in the presence of an alcoholic compound represented by the general formula (5);

$$R^3OH \quad (5)$$

wherein $R^3$ represents a substituted or unsubstituted alkyl group containing 1 to 20 carbon atoms, or a substituted or unsubstituted aralkyl group containing 7 to 30 carbon atoms.

4. The process for preparing optically active alcoholic compounds according to claim 3, wherein the alcoholic compound represented by the general formula (5) is isopropanol or benzhydrol.

5. A process for preparing optically active alcoholic compounds by conducting asymmetric reduction of a prochiral carbonyl compounds represented by the general formula (1);

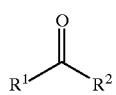
(1)

wherein $R^1$ and $R^2$ are different from each other and represent a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, a substituted or unsubstituted alkoxycarbonyl group containing 1 to 20 carbon atoms, or a cyano group, provided that at least one of $R^1$ and $R^2$ represents a substituted or unsubstituted alkyl group containing 1 to 20 carbon atoms, a substituted or unsubstituted aralkyl group containing 7 to 30 carbon atoms, or a substituted or unsubstituted aryl group containing 6 to 30 carbon atoms; and $R^1$ and $R^2$ may link together and form a substituted or unsubstituted ring;

to thereby prepare an optically active alcoholic compound represented by the general formula (3);

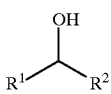

(3)

wherein $R^1$ and $R^2$ are the same as defined above;
which comprises treating the carbonyl compounds represented by the general formula (1) with a reducing agent prepared by treating an aluminum compound of the general formula (6);

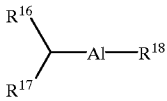

(6)

wherein $R^{16}$, $R^{17}$ and $R^{18}$ are the same or different from each other and represent an alkyl group containing 1 to 20 carbon atoms, an aralkyl group containing 7 to 30 carbon atoms, an aryl group containing 6 to 30 carbon atoms, an alkoxyl group containing 1 to 20 carbon atoms, or a hydrogen atom; with an optically active bisalcohol derivative represented by the general formula (7);

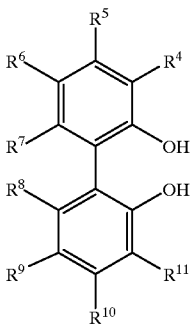

(7)

wherein $R^4$, $R^5$, $R^6$, $R^7$, $R^8$, $R^9$, $R^{10}$ and $R^{11}$ are the same or different from each other and represent a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, a substituted or unsubstituted silyl group, a substituted or unsubstituted amino group, a substituted or unsubstituted alkoxyl group containing 1 to 20 carbon atoms, a cyano group, an alkoxycarbonyl group containing 1 to 20 carbon atoms, a substituted or unsubstituted phosphorus atom, a substituted or unsubstituted sulfur atom, a halogen atom, or a hydrogen atom, and $R^4$, $R^5$, $R^6$, $R^7$, $R^8$, $R^9R^{10}$ or $R^{11}$ may link with each of them and form a substituted or unsubstituted, condensed ring;
and with an alcoholic compound represented by the general formula (5);

$$R^3OH \quad (5)$$

wherein $R^3$ represents a substituted or unsubstituted alkyl group containing 1 to 20 carbon atoms, or a substituted or unsubstituted aralkyl group containing 7 to 30 carbon atoms.

6. The process for preparing optically active alcoholic compounds according to claim 5, wherein the aluminum compound represented by the general formula (6) is triisobutylaluminum, diisobutylaluminum halide or aluminum triisopropoxide, and the alcoholic compound represented by the general formula (5) is isopropanol or benzhydrol.

7. The process for preparing optically active alcoholic compounds according to claim 1, wherein the prochiral carbonyl compound represented by the general formula (1) is a prochiral carbonyl compound represented by the general formula (8);

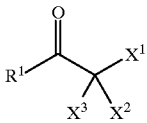

(8)

wherein $R^1$ is the same as defined above; and $X^1$, $X^2$ and $X^3$ are the same or different from each other and represent a halogen atom, a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, or a hydrogen atom, provided that at least one of $X^1$, $X^2$ and $X^3$ is a halogen atom;
and the optically active alcoholic compound represented by the general formula (3) is an optically active halohydrin derivative represented by the general formula (9);

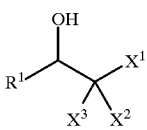

(9)

wherein $R^1$, $X^1$, $X^2$ and $X^3$ are the same as defined above.

8. The process for preparing optically active alcoholic compounds according to claim 2, wherein the prochiral carbonyl compound represented by the general formula (1) is a prochiral carbonyl compound represented by the general formula (8);

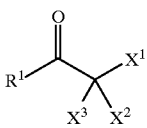

(8)

wherein $R^1$ is the same as defined above; and $X^1$, $X^2$ and $X^3$ are the same or different from each other and represent a halogen atom, a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, or a hydrogen atom, provided that at least one of $X^1$, $X^2$ and $X^3$ is a halogen atom;
and the optically active alcoholic compound represented by the general formula (3) is an optically active halohydrin derivative represented by the general formula (9);

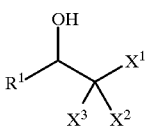

(9)

wherein $R^1$, $X^1$, $X^2$ and $X^3$ are the same as defined above.

9. The process for preparing optically active alcoholic compounds according to claim 3, wherein the prochiral carbonyl compound represented by the general formula (1) is a prochiral carbonyl compound represented by the general formula (8);

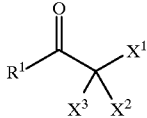
(8)

wherein $R^1$ is the same as defined above; and $X^1$, $X^2$ and $X^3$ are the same or different from each other and represent a halogen atom, a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, or a hydrogen atom, provided that at least one of $X^1$, $X^2$ and $X^3$ is a halogen atom;

and the optically active alcoholic compound represented by the general formula (3) is an optically active halohydrin derivative represented by the general formula (9);

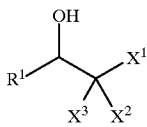
(9)

wherein $R^1$, $X^1$, $X^2$ and $X^3$ are the same as defined above.

10. The process for preparing optically active alcoholic compounds according to claim 4, wherein the prochiral carbonyl compound represented by the general formula (1) is a prochiral carbonyl compound represented by the general formula (8);

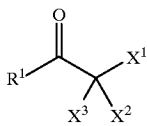
(8)

wherein $R^1$ is the same as defined above; and $X^1$, $X^2$ and $X^3$ are the same or different from each other and represent a halogen atom, a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, or a hydrogen atom, provided that at least one of $X^1$, $X^2$ and $X^3$ is a halogen atom;

and the optically active alcoholic compound represented by the general formula (3) is an optically active halohydrin derivative represented by the general formula (9);

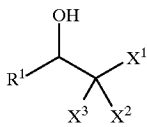
(9)

wherein $R^1$, $X^1$, $X^2$ and $X^3$ are the same as defined above.

11. The process for preparing optically active alcoholic compounds according to claim 5, wherein the prochiral carbonyl compound represented by the general formula (1) is a prochiral carbonyl compound represented by the general formula (8);

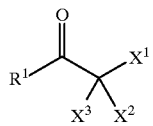
(8)

wherein $R^1$ is the same as defined above; and $X^1$, $X^2$ and $X^3$ are the same or different from each other and represent a halogen atom, a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, or a hydrogen atom, provided that at least one of $X^1$, $X^2$ and $X^3$ is a halogen atom;

and the optically active alcoholic compound represented by the general formula (3) is an optically active halohydrin derivative represented by the general formula (9);

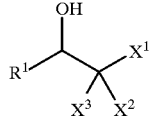
(9)

wherein $R^1$, $X^1$, $X^2$ and $X^3$ are the same as defined above.

12. The process for preparing optically active alcoholic compounds according to claim 6, wherein the prochiral carbonyl compound represented by the general formula (1) is a prochiral carbonyl compound represented by the general formula (8);

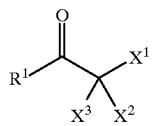
(8)

wherein $R^1$ is the same as defined above; and $X^1$, $X^2$ and $X^3$ are the same or different from each other and represent a halogen atom, a substituted or unsubstituted alkyl group containing 1 to 20 carbon atoms, a substituted or unsubstituted aralkyl group containing 7 to 30 carbon atoms, a substituted or unsubstituted aryl group containing 6 to 30 carbon atoms, or a hydrogen atom, provided that at least one of $X^1$, $X^2$ and $X^3$ is a halogen atom;

and the optically active alcoholic compound represented by the general formula (3) is an optically active halohydrin derivative represented by the general formula (9);

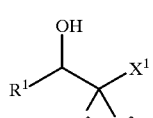
(9)

wherein $R^1$, $X^1$, $X^2$ and $X^3$ are the same as defined above.

* * * * *

UNITED STATES PATENT AND TRADEMARK OFFICE
CERTIFICATE OF CORRECTION

PATENT NO.    : 6,187,966 B1
DATED         : February 13, 2001
INVENTOR(S)   : Tadashi Sugawa et al.

It is certified that error appears in the above-identified patent and that said Letters Patent is hereby corrected as shown below:

<u>Title page,</u>
Item [86], § 371 Date should read -- July 15, 1999 --.
Item [86], § 102(e) Date sould read -- July 15, 1999 --.

Signed and Sealed this

Second Day of October, 2001

Attest:

*Nicholas P. Godici*

NICHOLAS P. GODICI
*Attesting Officer*  *Acting Director of the United States Patent and Trademark Office*